United States Patent [19]

Hamaguchi et al.

[11] Patent Number: 4,588,694

[45] Date of Patent: May 13, 1986

[54] PROCESS FOR PRODUCTION OF OPTICALLY ACTIVE OXAZOLIDINONE DERIVATIVE

[75] Inventors: Shigeki Hamaguchi, Kobe; Hiroshi Yamamura, Takasago; Junzo Hasegawa, Akashi; Hajime Kawaharada, Kakogawa; Kiyoshi Watanabe, Akashi, all of Japan

[73] Assignee: Kanegafuchi Kagaku Kogyo Kabushiki Kaisha, Osaka, Japan

[21] Appl. No.: 522,687

[22] Filed: Aug. 12, 1983

[30] Foreign Application Priority Data

Aug. 13, 1982 [JP] Japan .................. 57-141575

[51] Int. Cl.$^4$ ............................................. C07B 19/02
[52] U.S. Cl. ...................................... 435/280; 435/121
[58] Field of Search ................................... 435/280

[56] References Cited

U.S. PATENT DOCUMENTS

| | | | |
|---|---|---|---|
| 3,607,651 | 9/1971 | Moroe | 435/280 |
| 3,919,239 | 11/1975 | Nakagawa | 546/158 |
| 4,332,905 | 6/1982 | Olivieri | 435/280 |
| 4,461,835 | 7/1984 | Sih | 435/280 |
| 4,481,362 | 11/1984 | Nakai | 435/280 |
| 4,489,208 | 12/1984 | Olivieri | 560/157 X |

FOREIGN PATENT DOCUMENTS 0015418 9/1980 European Pat. Off. .
1470030 4/1977 United Kingdom .

OTHER PUBLICATIONS

Tsuda, Yoshisuke et al., Chem. Pharm. Bull., vol. 29, No. 19, pp. 3593–3600, 1981.

*Primary Examiner*—Sidney Marantz
*Assistant Examiner*—Jeremy Jay
*Attorney, Agent, or Firm*—Antonelli, Terry & Wands

[57] ABSTRACT

A process for preparing the optically active oxazolidinone derivative [(S)-I] by utilizing microorganisms or enzymes having a stereoselective esterase activity capable of asymmetrically hydrolyzing the racemates of the acyloxyoxazolidinone derivative [(R,S)-II], by separating the unreacted compound [(S)-II] from the hydrolyzed compound [(R)-I] and by hydrolyzing the compound [(S)-II]. The compounds are useful as intermediates for preparing optically active $\beta$-adrenergic blocking agents.

23 Claims, No Drawings

PROCESS FOR PRODUCTION OF OPTICALLY ACTIVE OXAZOLIDINONE DERIVATIVE

BACKGROUND OF THE INVENTION

The present invention relates to a process for production of optically active oxazolidinone derivatives. More particularly, the present invention relates to production of an optically active (S)-(+)-3-alkyl-5-acyloxymethyloxazolidin-2-one having the formula [(S)-II]:

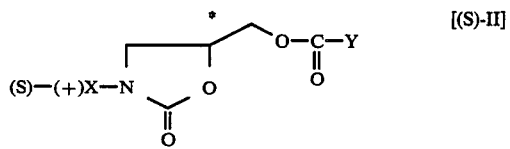

wherein X is a lower alkyl group and Y is a substituted or unsubstituted alkyl group, an alkenyl group, or a substituted or unsubstituted aromatic hydrocarbon group, and an optically active (S)-(+)-3-alkyl-5-hydroxymethyloxazolidin-2-one having the formula [(S)-I]:

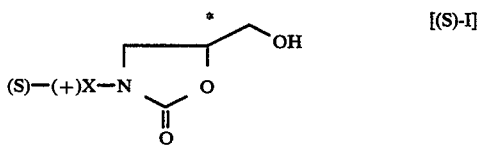

wherein X is as described above, by utilizing the action of a microorganism or an enzyme derived from the microorganism, i.e. the microorganism and enzyme having a stereoselective esterase activity.

The compounds [(S)-II] and [(S)-I] are important intermediates for preparing optically active β-adrenergic blocking agents (hereinafter referred to as "β-blockers").

As processes for preparing optically active β-blockers, there hitherto have been known the following methods:

(1) A method in which a racemate of β-blocker is optically resolved, as disclosed in Japanese Unexamined Patent Publication No. 149233/1980 and U.S. Pat. No. 3,655,663.

(2) A method in which an optically active β-blocker is prepared from an optically active 3-alkylamino-1,2-propanediol obtained by optical resolution of the racemate thereof, as disclosed in Japanese Unexamined Patent Publication No. 118,711/1976.

(3) A method in which an optically active β-blocker is prepared from D-mannitol via D-glycerol acetonide, as disclosed in Journal of Organic Chemistry, 41 (b 19), 3121 to 3124 (1976); Chemical and Pharmaceutical Bulletin, 29 (12), 3593 to 3600 (1981).

However, the method (1) is disadvantageous from the economical point of view because the final product of the racemate is optically resolved. The method (2) cannot easily provide an optically active 3-alkylamino-1,2-propanediol in high yield and high purity by using an optical resolution, because the 3-alkylamino-1,2-propanediol is hygroscopic and poor in crystallization. And the method (3) requires a large amount of lead tetraacetate for preparing D-glycerol acetonide from D-mannitol, and accordingly is not suitable for the industrial production. Thus, these processes include economical or practical problems, and there has not been industrially advantageous process for the production of optically active β-blockers.

On the other hand, the following reaction pathway is known as a rational synthetic pathway for preparing optically active β-blockers, as disclosed in Yoshisuke Tsuda et al: Chemical and Pharmaceutical Bulletin, 29 (12), 3593 to 3600 (1981); Canadian Pat. No. 965,787.

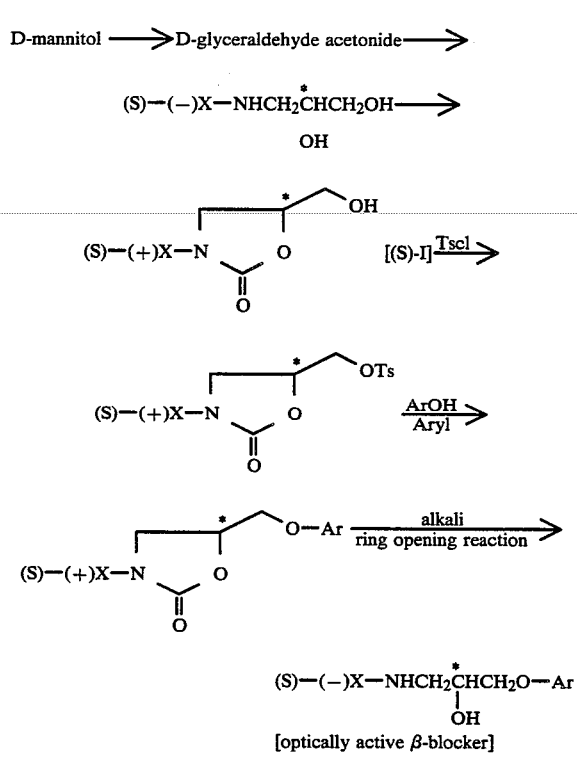

[optically active β-blocker]

wherein X is as described above, Ar is an aryl derivative.

It is an object of the present invention to provide novel and simple processes for producing the compound [(S)-I]. Another object of the present invention is to provide novel and simple processes for producing the compound [(S)-II] which is a useful intermediate for producing the compound [(S)-I].

SUMMARY OF THE INVENTION

The present inventors have considered that a (R,S)-(±)-3-alkyl-5-acyloxymethyloxazolidin-2-one can be easily prepared from a (R,S)-(±)-3-alkyl-5-hydroxymethyloxazolidin-2-one by esterifying and that an optically active (S)-(+)-3-alkyl-5-hydroxymethyloxazolidin-2-one having the formula [(S)-I] can be prepared from the above (R,S)-(±)-3-alkyl-5-acyloxymethyloxazolidin-2-one by the stereoselective hydrolysis using a microorganism or an enzyme. As a result of various studies, the present inventors have now found microorganisms and enzymes having a stereoselective esterase activity capable of asymmetrically hydrolyzing the racemic compound (R,S)-(±)-3-alkyl-5-acyloxymethyloxazolidin-2-one so as to substantially produce an optically active (R)-(−)-3-alkyl-5-hydroxymethyloxazolidin-2-one, and further found that the compound [(S)-I] can be obtained by isolating the unreacted compound [(S)-II] through a simple procedure and hydrolyzing the compound [(S)-II].

In accordance with the present invention, there can be provided a process for producing an optically active (S)-(+)-3-alkyl-5-acyloxymethyloxazolidin-2-one which comprises subjecting a racemic compound of (R,S)-(±)-3-alkyl-5-acyloxymethyloxazolidin-2-one having the formula [(R,S)-II]:

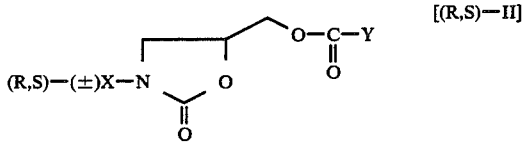

wherein X is a lower alkyl group and Y is a substituted or unsubstituted alkyl group, and alkenyl group, or a substituted or unsubstituted aromatic hydrocarbon group, to the action of a microorganism or an enzyme derived from the microorganism; i.e. the microorganism and enzyme having a stereoselective esterase activity capable of asymmetrically hydrolyzing the compound of (R)-(−)-3-alkyl-5-acyloxymethyloxazolidin-2-one having the formula [(R)-II]:

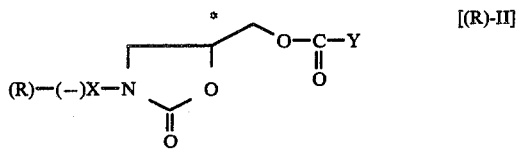

wherein X and Y are as defined above so as to substantially produce an optically active (R)-(−)-3-alkyl-5-hydroxymethyloxazolidin-2-one having the formula [(R)-I]:

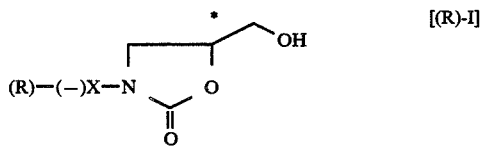

wherein X is as defined above, and isolating the unreacted optically active (S)-(+)-3-alkyl-5-acyloxymethyloxazolidin-2-one having the formula [(S)-II].

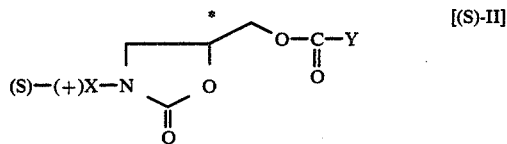

The optically active compound [(S)-II] is recovered by various methods such as extraction with an organic solvent, column chromatography and fractional distillation. The compound [(S)-II] can be easily converted into the optically active compound [(S)-I] by hydrolysis. Accordingly, the present invention also provides a process for preparing the optically active compound [(S)-I].

The summary of the pathway for obtaining the compound [(S)-I] is as follows:

[(R,S)-II] —enzymatic and asymmetric hydrolysis→

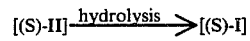

According to the present invention, optically active β-blockers can be synthesized in high purity and inexpensive by conventional methods by using the compound [(S)-I].

DETAILED DESCRIPTION

The substituent group defined as X in the formula [(R)-I], [(S)-I], [(R)-II], [(S)-II] or [(R,S)-II] or [(R)-II] is a lower alkyl group having 1 to 6 carbon atoms, such as methyl, ethyl, propyl, isopropyl, butyl or t-butyl group, preferably, isopropyl or t-butyl group. The substituent group defined as Y in the formula [(R,S)-II] is a substituted or unsubstituted alkyl group having 1 to 17, an alkenyl group having 2 to 8 carbon atoms, or a substituted or unsubstituted aromatic hydrocarbon group. More particularly, examples of the above Y are, for instance, an unsubstituted alkyl group such as methyl, ethyl, propyl or butyl group; a substituted alkyl group having a substituent group such as halogen, hydroxyl or alkoxy group, e.g. chloromethyl, dichloromethyl, trifluoromethyl or β,β,β-trichloroethoxymethyl group; an alkenyl group such as allyl group; an unsubstituted aryl group such as phenyl group; a substituted aryl group having a substituent group such as alkyl, halogen, hydroxyl or alkoxy group, e.g. p-methylphenyl, p-chlorophenyl or p-methoxyphenyl group; an unsubstituted aralkyl group such as benzyl group; a substituted aralkyl group having a substituent group such as alkyl, halogen, hydroxyl or alkoxy group, e.g. p-methylbenzyl, p-chlorobenzyl, p-hydroxybenzyl or p-methoxybenzyl group.

The microorganisms used in the present invention having the stereoselective esterase activity capable of asymmetrically hydrolyzing the compound [(R,S)-II] so as to substantially produce the compound [(R)-I] can be easily selected by the following screening method.

A representative example of the screening method is as follows: In case of using (R,S)-(±)-3-t-butyl-5-acetoxymethyloxazolidin-2-one as a substrate, first, a microorganism is cultured with shaking at a temperature of from 25° to 35° C. for 1 to 2 days in a large tube containing 10 ml of a culture medium in which the microorganism can grow. To the resulting culture broth is added 2% (w/v) of (R,S)-(±)-3-t-butyl-5-acetoxymethyloxazolidin-2-one and the mixture is incubated at a temperature of from 20° to 35° C. for 1 to 3 days. During the incubation, a pH of the mixture is kept between 5 and 7, and the amount of the substrate in the reaction mixture is assayed by gas chromatography (column: Silicone OV-17, 1 m×3 mmφ, Gaschro Kogyo INC.; column temperature: 180° C.). And a strain having a hydrolysis rate which is particularly slow down at the time when about 50% of the total amount of the substrate is hydrolyzed is primarily selected.

Further, the culture and hydrolysis are carried out by using the selected strain in the same manner as described above except that the scale of reaction increases by a volume of 400 ml. After completing the reaction, the mixture is extracted with 400 ml of ethyl acetate, and the extract is applied to a column of silica gel and eluted with a mixed solvent of hexane and acetone for separating the unreacted 3-t-butyl-5-acetoxymethyloxazolidin-2-one, and a fraction of 3-t-butyl-5-hydroxymethyloxazolidin-2-one is concentrated. When hexane is slowly added to the concentrate, a crystal is allowed to precipitate. After drying the precipitate under vacuum, it can be easily determined whether or not the used microorganism has a stereoselective esterase activity by measuring a specific optical rotatory power of the precipitate.

An enzyme having a stereoselective esterase activity capable of asymmetrically hydrolyzing the compound [(R,S)-II] can be also selected in the same screening method as in the selection of a microorganism except that a cell-free enzyme extract prepared by centrifuging the homogenized suspension of the microorganism, a partially purified enzyme prepared by fractionating the cell-free enzyme extract or a commercially available enzyme is used instead of a cell suspension. In that case, the stereoselective esterase activity which is undetectable or hard to detect by using a cell suspension can be detected.

The microorganisms used in the present invention, having a stereoselective esterase activity capable of asymmetrically hydrolyzing the compound [(R,S)-II] so as to substantially produce the compound [(R)-I] are selected from bacteria, yeasts, molds, and the like. Examples of the genera of the microorganisms are, for instance, Enterobacter, Klebsiella, Micrococcus, Citrobacter, Escherichia, Pseudomonas, Staphylococcus, Alcaligenes, Achromobacter, Streptomyces, Candida, Debaryomyces, Endomyces, Hansenula, Geotrichum, Kluyveromyces, Metschnikowia, Pichia, and the like. Examples of the strains of the microorganisms are, for instance, *Enterobacter aerogenes* IFO 12010, IFO 13534; *Enterobacter cloacae* IFO 3320, IFO 12935; *Klebsiella pneumoniae* IFO 3318, IFO 3321; *Micrococcus luteus* IFO 3064, IFO 3066; *Citrobacter freundii* IFO 12681; *Escherichia coli* IFO 3366; *Pseudomonas cruciviae* IFO 12047; *Pseudomonas fluorescens* IFO 3081; *Staphylococcus aureus* IFO 3761; *Alcaligenes faecalis* IFO 12669; *Achromobacteria parvulus* IFO 13182; *Streptomyces flavovirens* IFO 3412; *Streptomyces aureus* IFO 3175; *Candida pseudotropicalis* IFO 0432; *Candida Kefyr* IFO 0008; *Debaryomyces hansenii* IFO 0017, IFO 0034; *Endomyces geotrichum* CBS 178.71; *Hansenula anomala* IFO 0144, *Hansenula minuta* IFO 0975; *Geotrichum candidum* CBS 187.67, *Kluyveromyces fragilis* IFO 0288, IFO 0541; *Metschnikowia pulcherrima* IFO 0561; *Pichia farinosa* IFO 0459, *Pichia membranaefaciens* IFO 0186, and the like.

For culture of the above microorganisms, any medium in which they can grow can be used. The media usually contain an organic and inorganic carbon source and nitrogen source, and if necessary, vitamins, mineral, and so on. The culture is carried out at a temperature of from 20° to 40° C. and a pH of from 3 to 11, preferably from 4 to 8, and if necessary, the culture is aerobically carried out with shaking for stimulating a growth of the microorganism.

For asymmetric hydrolysis reaction of the compound [(R,S)-II], the compound [(R,S)-II] is added to a culture medium at the beginning of the culture so as to simultaneously carry out the culture and the hydrolysis, or the compound [(R,S)-II] is subjected to the action of a cultured broth so as to carry out the hydrolysis as mentioned above. A hydrolysis method, in which the compound [(R,S)-II] is added to a cell suspension with a high concentration obtained by centrifugation, and so on, is preferred in point of recovering the products after the hydrolysis.

On the other hand, a cell-free enzyme extract prepared by centrifuging the homogenized suspension of the microorganism as described above can be used for the stereoselective hydrolysis of the compound [(R,S)-II]. And also a commercially available emzyme prepared from microorganisms can be used for the stereoselective hydrolysis of the compound [(R,S)-II]. For example, stereoselective L.P.L. "Amano" (lipoprotein lipase from Pseudomonas, Amano Pharmaceutical Co., Ltd.), Lipase PL 266 (from Alcaligenes, Meito Sangyo Co., Ltd.), or Lipase AL (from Achromobacter, Meito Sangyo Co., Ltd.). An immobilized form of the microorganisms or the enzymes is also available for the stereoselective hydrolysis of the compound [(R,S)-II] instead of the free microorganisms described above.

The concentration of the compound [(R,S)-II] in the reaction mixture may be varied from 0.1% by weight to a concentration as high as 30% by weight.

Though the compound [(R,S)-II] has a a poor solubility in water, it is not an obstacle to the hydrolysis reaction by sufficiently contacting the compound [(R,S)-II] with the microorganism or enzyme with shaking. And a hydrophilic solvent such as acetone or a surface-active agent may be added to the reaction mixture in an amount which does not affect the reaction.

The hydrolysis reaction is preferably carried out at a pH of from 4 to 8.

When the compound [(R,S)-II] is hydrolyzed in a high concentration, it is preferred to maintain the optimal pH with a suitable neutralizing agent such as a sodium hydroxide solution, since the hydrolyzed organic acid is gradually accumulated in the reaction mixture and the pH of the reaction mixture is converted to acidic side. The hydrolysis reaction is carried out at a temperature suitable to the utilized microorganism, generally at a temperature of from 10° to 50° C.

The separation and recovery of the unreacted compound [(S)-II] from the produced organic acid and the compound [(R)-I] can be carried out by a conventional purification method. An example of the method is as follows: After removing the insoluble materials such as cells from the reaction mixture by centrifugation, the reaction mixture is extracted with an organic solvent usually used, such as hexane, cyclohexane, ether, butyl acetate, chloroform, dichloromethane, benzene or toluene and the extract is concentrated under a reduced pressure to obtain the unreacted compound [(S)-II].

However, the unreacted compound [(S)-II] is not completely separated from the produced organic acid and the compound [(R)-I] by the above-mentioned solvent extraction method, when the substituent group defined as Y in the formula [(S)-II] is a lower alkyl group such as methyl, ethyl or propyl group. In that case, after removing the insoluble materials in the same manner as described above, the reaction mixture is extracted with an organic solvent such as ethyl acetate and the extract is concentrated under a reduced pressure. The concentrate is subjected to column chromatography to easily separate and recover the compound [(S)-II]. The column chromatography is carried out by using a conventional carrier such as silica gel, alumina or florisil. On the other hand, the compound [(S)-II] also can be easily separated and recovered by a fractional distillation procedure when there is a difference between the reflux temperature of the compounds [(S)-II] and [(R)-I].

The compound [(S)-II] can be converted into the compound [(S)-I by the following hydrolysis method.

For example, a chemical hydrolysis method in which the compound [(S)-II] is suspended in water and allowed to stand at a room temperature for several hours while adjusting a pH of the mixture in the range of 8 to 14, preferably 12 to 13.5, with a suitable neutralizing agent such as a sodium hydroxide solution, or an enzymatic hydrolysis method in which the compound [(S)-II] is subjected to the action of a non-stereoselective hydrolase, e.g. a lipase (steapsin), an esterase such as one derived from a hog liver, at a temperature of from 20° to 40° C. while adjusting a pH of the mixture in the range of 4 to 8. Then, the crystal of the compound [(S)-I] can be obtained by extracting the produced compound [(S)-I] with an organic solvent such as ethyl acetate, and concentrating the extract under a reduced pressure.

The compound [(S)-I] can be easily converted into various kinds of β-blockers by conventional methods such as those shown as follows:

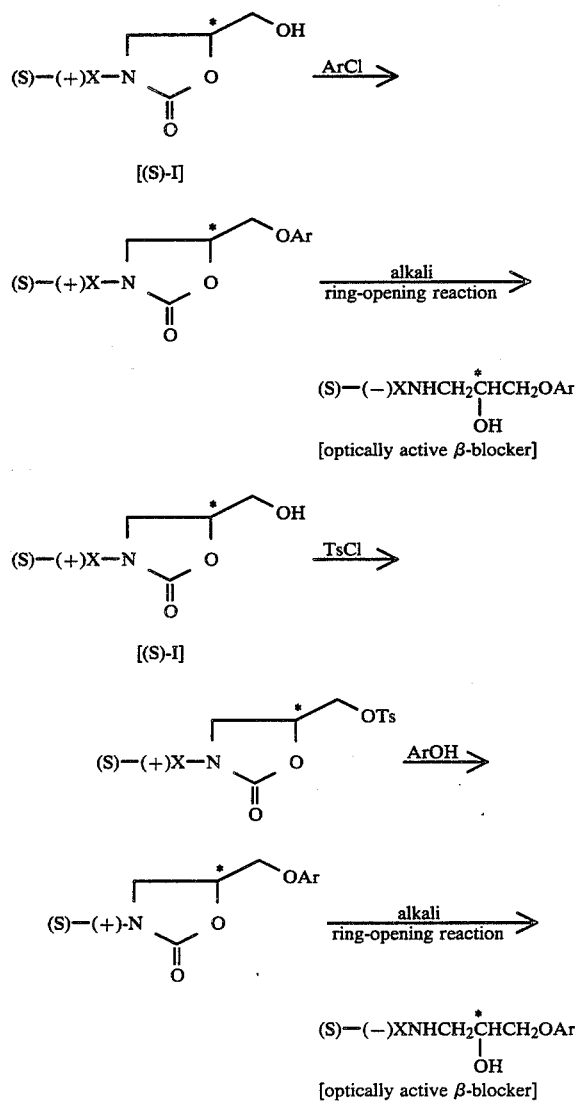

wherein Ar is an aryl derivative, X is as defined above.

The present invention is more particularly described and explained by means of the following Examples, in which all % are by weight unless otherwise noted. These examples are intended to illustrate the invention and not to be construed to limit the scope of the invention.

Also, the microorganisms utilized in the following Examples are all previously known, and strains marked with IFO or CBS are those deposited in the following depositories under the shown catalogue numbers.
IFO: Institute for Fermentation, Osaka (Japan)
CBS: Centraal Bureau voor Schimmelcurtures (Netherlands)

EXAMPLE 1

The medium of the following components was prepared, and 400 ml portions thereof were separately placed in 2 l of a Sakaguchi flask and steam-sterilized at 120° C. for 15 minutes.

| [Medium components] | |
|---|---|
| Glucose | 4.0% |
| Yeast extract | 0.3% |
| Meat extract | 0.3% |
| Peptone | 0.3% |
| (NH$_4$)$_2$HPO$_4$ | 0.2% |
| KH$_2$PO$_4$ | 0.1% |
| pH | 7.0 |

On the other hand, *Enterobacter aerogenes* IFO 12010 was previously cultured in the medium containing the same components as described above, and then 10 ml portions thereof were separately inoculated into the above medium and cultured with shaking at 30° C. for 24 hours. The cells were collected from 4 liters of the cultured broth by centrifugation and the cells were suspended in 400 ml of 0.1M phosphate buffer of pH 7.0 and 40 g of (R,S)-(±)-3-t-butyl-5-acetoxymethyloxazolidin-2-one having the formula:

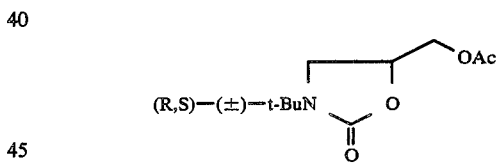

was added to the suspension as a substrate. The thus obtained mixture was incubated in 1 l of a vessel with stirring at 30° C. for 18 hours while adjusting a pH of the mixture in the range of 5 to 7 with a sodium hydroxide solution.

After completing the reaction, the resulting supernatant obtained by centrifugation was extracted twice with each 400 ml of ethyl acetate, and then the extract was concentrated under a reduced pressure.

The obtained concentrate was chromatographed on a column of silica gel, and the fractions of (S)-(+)-3-t-butyl-5-acetoxymethyloxazolidin-2-one eluted with a mixed solvent of hexane-acetone (3:1 by v/v) were gathered and concentrated under a reduced pressure. After removing the solvent, 18.5 g of colorless oily material was obtained. The value of a specific optical rotatory power is $[\alpha]_D^{16}+36.3°$ (C=1.0, chloroform), and the NMR spectrum is as follows:

$^1$H-NMR (90 MHz, in CDCl$_3$) δ(ppm): 1.4 (9H, s, C(CH$_3$)$_3$), 2.1

(3H, s, 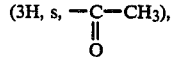), 3.3–3.8 (2H, m, —CH$_2$N—), 4.1–4.25 (2H, m, —CH$_2$O—), 4.4–4.7 (1H, m, —CH$_2$CH(O—)CH$_2$).

The thus obtained (S)-(+)-3-t-butyl-5-acetoxymethyloxazolidin-2-one was suspended in 100 ml of water, and the resulting mixture was hydrolyzed at a room temperature for two days while adjusting a pH of the mixture in the range of 10 to 12 with a sodium hydroxide solution.

After completing the hydrolysis, the mixture was extracted with 200 ml of ethyl acetate, and the resulting extract was dehydrated, and then concentrated under a reduced pressure. When hexane was slowly added to the concentrate, a colorless crystal was allowed to precipitate. The precipitated crystal was dried under vacuum to give 12.9 g of (S)-(+)-3-t-butyl-5-hydroxymethyloxazolidin-2-one having a specific optical rotatory power of $[\alpha]_D^{16}$+46.0° (C=1.0, chloroform).

The result of NMR spectrum is as follows: $^1$H-NMR (90 MHz, in CDCl$_3$) δ(ppm): 1.4 (9H, s, C(CH$_3$)$_3$), 3.4–3.95 (5H, —CH$_2$N—, —CH$_2$O—, —OH), 4.3–4.6 (1H, m, —CH$_2$CH(O—)CH$_2$—).

EXAMPLES 2 TO 14

The procedure of Example 1 was repeated except that the strain of microorganism was changed as shown in Table 1. The results are shown in Table 1.

TABLE 1

Substrate: (R,S)—(±)-3-t-butyl-5-acetoxymethyloxazolidin-2-one

| Example | Strain | (S)—(+)-3-t-butyl-5-acetoxy-methyloxazolidin-2-one | | (S)—(+)-3-t-butyl-5-hydroxy-methyloxazolidin-2-one | |
|---|---|---|---|---|---|
| | | Yield g | $[\alpha]_D^{16}$ (C = 1.0, chloroform) | Yield g | $[\alpha]_D^{16}$ (C = 1.0, chloroform) |
| 2 | Enterobacter aerogenes IFO 13534 | 17.8 | +36.4° | 12.5 | +46.2° |
| 3 | Enterobacter cloacae IFO 3320 | 16.8 | +36.1° | 11.8 | +45.8° |
| 4 | Enterobacter cloacae IFO 12935 | 16.5 | +35.9° | 11.4 | +45.6° |
| 5 | Klebsiella pneumoniae IFO 3318 | 17.2 | +37.0° | 11.9 | +47.0° |
| 6 | Klebsiella pneumoniae IFO 3321 | 17.6 | +36.8° | 12.2 | +46.8° |
| 7 | Micrococcus luteus IFO 3064 | 16.9 | +33.2° | 11.8 | +42.5° |
| 8 | Micrococcus luteus IFO 3066 | 17.1 | +32.9° | 11.9 | +41.8° |
| 9 | Escherichia coli IFO 3366 | 17.0 | +28.7° | 11.7 | +36.5° |
| 10 | Pseudomonas cruciviae IFO 12047 | 16.8 | +29.5° | 11.7 | +37.8° |
| 11 | Pseudomonas fluorescens IFO 3081 | 17.0 | +30.1° | 11.9 | +38.1° |
| 12 | Staphylococcus aureus IFO 3761 | 16.9 | +25.6° | 11.8 | +32.5° |
| 13 | Alcaligenes faecalis IFO 12669 | 17.1 | +21.9° | 12.0 | +28.1° |
| 14 | Achromobacter parvulus IFO 13182 | 17.2 | +18.4° | 11.8 | +23.4° |

EXAMPLES 15 TO 28

The procedure of Example 1 was repeated except that the strain of microorganism was changed as shown in Table 2 and (R,S)-(±)-3-isopropyl-5-acetoxymethyloxazolidin-2-one was employed as a substrate. The results are shown in Table 2.

The result of NMR spectrum of (S)-(+)-3-isopropyl-5-hydroxymethyloxazolidin-2-one is as follows: $^1$H-NMR (90 MHz, in CDCl$_3$) δ(ppm): 1.2 (6H, d, —CH(CH$_3$)$_2$), 3.4–4.2 (6H, m, —CH$_2$N—, —CH$_2$O (CH$_3$)$_2$CH—, —OH), 4.3–4.7 (1H, m, —CH$_2$CH(O—)CH$_2$—).

TABLE 2

Substrate: (R,S)—(±)-3-isopropyl-5-acetoxymethyloxazolidin-2-one

| Example | Strain | (S)—(+)-3-isopropyl-5-acetoxymethyloxa-zolidin-2-one | | (S)—(+)-3-isopropyl-5-hydroxymethyloxa-zolidin-2-one | |
|---|---|---|---|---|---|
| | | Yield g | $[\alpha]_D^{20}$ (C = 1.0, chloroform) | Yield g | $[\alpha]_D^{20}$ (C = 1.0, chloroform) |
| 15 | Enterobacter aerogenes IFO 12010 | 17.7 | +42.3° | 11.9 | +54.2° |
| 16 | Enterobacter aerogenes IFO 13534 | 17.1 | +42.7° | 11.5 | +54.7° |
| 17 | Enterobacter cloacae IFO 3320 | 16.9 | +42.9° | 11.3 | +54.9° |
| 18 | Enterobacter cloacae IFO 12935 | 17.0 | +43.0° | 11.4 | +55.0° |
| 19 | Klebsiella pneumoniae IFO 3318 | 17.1 | +43.3° | 11.5 | +55.4° |
| 20 | Klebsiella pneumoniae IFO 3321 | 17.2 | +43.0° | 11.6 | +55.1° |
| 21 | Micrococcus luteus IFO 3064 | 16.8 | +39.3° | 11.3 | +50.0° |
| 22 | Micrococcus luteus IFO 3066 | 16.5 | +38.9° | 11.1 | +49.8° |
| 23 | Escherichia coli IFO 3366 | 17.0 | +33.4° | 11.5 | +42.8° |
| 24 | Pseudomonas cruciviae IFO 12047 | 17.1 | +32.8° | 11.2 | +41.9° |
| 25 | Pseudomonas fluorescens IFO 3081 | 17.5 | +33.7° | 11.8 | +43.1° |
| 26 | Staphylococcus aureus IFO 3761 | 16.6 | +30.1° | 11.0 | +38.2° |
| 27 | Alcarigenes faecalis IFO 12669 | 17.3 | +24.9° | 11.4 | +31.9° |
| 28 | Achromobacter parvulus IFO 13182 | 17.0 | +21.0° | 10.9 | +27.0° |

EXAMPLE 29

The medium of the following components was prepared, and 400 ml portions thereof were separately placed in 2 l of a Sakaguchi flask and steam-sterilized at 120° C. for 15 minutes.

| [Medium components] | |
|---|---|
| Glucose | 2.0% |
| Yeast extract | 0.3% |
| (NH$_4$)$_2$HPO$_4$ | 1.3% |

-continued

| [Medium components] | |
|---|---|
| KH$_2$PO$_4$ | 0.7% |
| NaCl | 0.1% |
| ZnSO$_4$.7H$_2$O | 0.006% |
| FeSO$_4$.7H$_2$O | 0.009% |
| pH | 6.5 |

On the other hand, *Candida pseudotropicalis* IFO 0432 was previously cultured in the medium containing the same components as described above, and then 10 ml portions thereof were separately inoculated into the above medium and cultured with shaking at 30° C. for 24 hours. The cells were collected from 4 liters of the cultured broth by centrifugation and the cells were suspended in 400 ml of 0.1M phosphate buffer by pH 7.0, and 40 g of (R,S)-(±)-3-t-butyl-5-acetoxymethyloxazolidin-2-one having the formula:

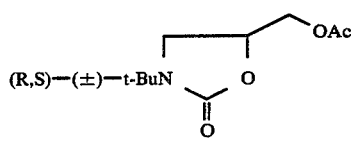

was added to the mixture as a substrate. The thus obtained mixture was subjected to reaction in 1 l of a vessel with stirring at 30° C. for 18 hours while adjusting a pH of the mixture in the range of 5 to 7 with a sodium hydroxide solution. After completing the reaction, the supernatant obtained by centrifugation was extracted twice with each 400 ml of ethyl acetate, and then the extract was concentrated under a reduced pressure.

The thus obtained concentrate was chromatographed on a column of silica gel, and the fraction of (S)-(+)-3-t-butyl-5-acetoxymethyloxazolidin-2-one eluted with a mixed solvent of hexane-acetone (3:1, v/v) were gathered and concentrated under a reduced pressure. After removing the solvent, 17.5 g of colorless oily material was obtained. The value of a specific optical rotatory power is $[\alpha]_D^{16}+24.5°$ (C=1.0, chloroform). The thus obtained (S)-(+)-3-t-butyl-5-acetoxymethyloxazolidin-2-one was suspended in 100 ml of water, and the resulting mixture was hydrolyzed at a room temperature for two days while adjusting a pH of the mixture in the range of 10 to 12 with a sodium hydroxide solution.

After completing the hydrolysis, the mixture was extracted with 200 ml of ethyl acetate, and the extract was dehydrated, and then concentrated under a reduced pressure. When hexane was added to the concentrate, a colorless crystal was allowed to precipitate. The precipitated crystal was gathered and dried under vacuum to give 11.5 g of (S)-(+)-3-t-butyl-5-hydroxymethyloxazolidin-2-one having a specific optical rotatory power of $[\alpha]_D^{16}+31.1°$ (C=1.0, chloroform).

EXAMPLES 30 TO 41

The procedure of Example 29 was repeated except that the strain of microorganism was changed as shown in Table 3. The results are shown in Table 3.

TABLE 3

| | Substrate: (R,S)—(±)-3-t-butyl-5-acetoxymethyloxazolidin-2-one | | | | |
|---|---|---|---|---|---|
| | | (S)—(+)-3-t-butyl-5-acetoxy-methyloxazolidin-2-one | | (S)—(+)-3-t-butyl-5-hydroxy-methyloxazolidin-2-one | |
| Example | Strain | Yield g | $[\alpha]_D^{16}$ (C = 1.0, chloroform) | Yield g | $[\alpha]_D^{16}$ (C = 1.0, chloroform) |
| 30 | *Candida kefyr* IFO 0008 | 16.2 | +24.5° | 10.5 | +31.0° |
| 31 | *Debaryomyces hansenii* IFO 0017 | 17.1 | +30.0° | 11.1 | +38.2° |
| 32 | *Debaryomyces hansenii* IFO 0034 | 16.3 | +29.3° | 10.6 | +37.5° |
| 33 | *Endomyces geotrichum* CBS 178.71 | 15.8 | +16.5° | 9.9 | +20.9° |
| 34 | *Hansenula anomala* IFO 0144 | 16.0 | +14.9° | 10.0 | +18.8° |
| 35 | *Hansenula minuta* IFO 0975 | 16.2 | +15.0° | 10.2 | +19.1° |
| 36 | *Geotrichum candidum* CBS 187.67 | 16.5 | +13.5° | 10.7 | +17.2° |
| 37 | *Kluyveromyces fragilis* IFO 0288 | 15.5 | +17.7° | 9.9 | +22.5° |
| 38 | *Kluyveromyces fragilis* IFO 0541 | 15.9 | +17.2° | 10.0 | +21.9° |
| 39 | *Metschnikowia pulcherrima* IFO 0561 | 16.4 | +24.1° | 10.5 | +30.8° |
| 40 | *Pichia farinosa* IFO 0459 | 17.0 | +26.4° | 11.0 | +33.5° |
| 41 | *Pichia membranaefaciens* IFO 0186 | 15.9 | +25.4° | 10.1 | +32.2° |

EXAMPLES 42 TO 54

The procedure of Example 29 was repeated except that the strain of microorganism was changed as shown in Table 4 and (R,S)-(±)-3-isopropyl-5-acetoxymethyloxazolidin-2-one was employed as a substrate. The results are shown in Table 4.

TABLE 4

| | Substrate: (R,S)—(±)-3-isopropyl-5-acetoxymethyloxazolidin-2-one | | | | |
|---|---|---|---|---|---|
| | | (S)—(+)-3-isopropyl-5-acetoxymethyloxa-zolidin-2-one | | (S)—(+)-3-isopropyl-5-hydroxymethyloxa-zolidin-2-one | |
| Example | Strain | Yield g | $[\alpha]_D^{20}$ (C = 1.0, chloroform) | Yield g | $[\alpha]_D^{20}$ (C = 1.0, chloroform) |
| 42 | *Candida pseudotropicalis* IFO 0432 | 17.2 | +29.0° | 11.1 | +37.1° |
| 43 | *Candia kefyr* IFO 0008 | 15.5 | +29.1° | 10.0 | +37.2° |
| 44 | *Debaryomyces hansenii* IFO 0017 | 16.0 | +35.7° | 10.3 | +45.7° |
| 45 | *Debaryomyces hansenii* IFO 0034 | 16.2 | +35.4° | 10.5 | +44.9° |
| 46 | *Endomyces geotrichum* CBS 178.71 | 15.4 | +19.7° | 9.4 | +25.0° |
| 47 | *Hansenula anomala* IFO 0144 | 15.6 | +17.4° | 9.8 | +22.1° |
| 48 | *Hansenula minuta* IFO 0975 | 15.8 | +18.0° | 9.7 | +22.9° |
| 49 | *Geotrichum candidum* CBS 187.67 | 15.1 | +16.1° | 9.2 | +20.5° |

TABLE 4-continued

| | Substrate: (R,S)—(±)-3-isopropyl-5-acetoxymethyloxazolidin-2-one | | | |
|---|---|---|---|---|
| | (S)—(+)-3-isopropyl-5-acetoxymethyloxa-zolidin-2-one | | (S)—(+)-3-isopropyl-5-hydroxymethyloxa-zolidin-2-one | |
| Example Strain | Yield g | $[\alpha]_D^{20}$ (C = 1.0, chloroform) | Yield g | $[\alpha]_D^{20}$ (C = 1.0, chloroform) |
| 50 Kluyveromyces fragilis IFO 0288 | 14.8 | +21.3° | 9.6 | +27.0° |
| 51 Kluyveromyces fragilis IFO 0541 | 14.2 | +20.5° | 9.2 | +26.3° |
| 52 Metschnikowia pulcherrima IFO 0561 | 15.6 | +29.1° | 9.3 | +36.9° |
| 53 Pichia farinosa IFO 0459 | 15.9 | +31.5° | 9.9 | +40.0° |
| 54 Pichia membranaefaciens IFO 0186 | 16.2 | +30.5° | 10.2 | +38.5° |

EXAMPLE 55

The medium of the following components was prepared, and 400 ml portions thereof were separately placed in 2 l of a Sakaguchi flask and steam-sterilized at 120° C. for 15 minutes.

| [Medium components] | |
|---|---|
| Glucose | 2.0% |
| Glycerol | 2.0% |
| Soybean meal | 3.0% |
| Yeast extract | 0.3% |
| Vitamin B$_{12}$ | 1 ppm |
| pH | 7.2 |

On the other hand, *Streptomyces flavovirens* IFO 3412 was previously cultured in the medium containing the same components as described above, and then 10 ml portions thereof were separately inoculated into the above medium and cultured with shaking at 30° C. for 48 hours.

The cells were collected from 4 liters of the cultured broth by centifugation and the cells were suspended in 400 ml of 0.1M phosphate buffer of pH 7.0, and 40 g of (R,S)-(±)-3-t-butyl-5-acetoxymethyloxazolidin-2-one having the formula:

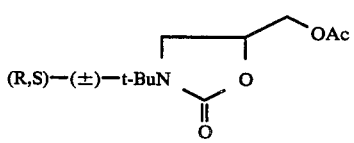

was added to the suspension as a substrate. The thus obtained mixture was subjected to reaction in 1 l of a vessel with stirring at 30° C. for 18 hours while adjusting pH of the mixture in the range of 5 to 7 with a sodium hydroxide solution. After completing the reaction, the supernatant obtained by centrifugation was extracted twice with each 400 ml of ethyl acetate, and then the extract was concentrated under a reduced pressure.

The obtained concentrate was chromatographed on a column of silica gel, and the fractions of (S)-(+)-3-t-butyl-5-acetoxymethyloxazolidin-2-one eluted with a mixed solvent of hexane-acetone (3:1 v/v) were gathered and concentrated under a reduced pressure. After removing the solvent, 16.9 g of colorless oily material was obtained. The value of a specific optical rotatory power is $[\alpha]_D^{16}+22.6°$ (C=1.0, chloroform).

The thus obtained (S)-(+)-3-t-butyl-5-acetoxymethyloxazolidin-2-one was suspended in 100 ml of water, and the resulting mixture was hydrolyzed at a room temperature for two days while adjusting a pH of the mixture in the range of 10 to 12 with a sodium hydroxide solution.

After completing the hydrolysis, the mixture was extracted with 200 ml of ethyl acetate, and the extract was dehydrated, and then concentrated under a reduced pressure. When hexane was slowly added to the concentrate, a colorless crystal was allowed to precipitate. The precipitated crystal was gathered and dried under vacuum to give 11.1 g of (S)-(+)-3-t-butyl-5-hydroxymethyloxazolidin-2-one having specific optical rotatory power of $[\alpha]_D^{16}+28.7$ (C=1.0, chloroform).

EXAMPLE 56

The procedure of Example 51 was repeated except that the strain of microorganism was changed as shown in Table 5. The results are shown in Table 5.

TABLE 5

| | Substrate: (R,S)—(±)-3-t-butyl-5-acetoxymethyloxazolidin-2-one | | | |
|---|---|---|---|---|
| | (S)—(+)-3-t-butyl-5-acetoxy-methyloxazolidin-2-one | | (S)—(+)-3-t-butyl-5-hydroxy-methyloxazolidin-2-one | |
| Example Strain | Yield g | $[\alpha]_D^{16}$ (C = 1.0, chloroform) | Yield g | $[\alpha]_D^{16}$ (C = 1.0, chloroform) |
| 56 Staphylococcus aureus IFO 3175 | 16.8 | +16.0° | 11.0 | +21.0° |

EXAMPLES 57 TO 58

The procedure of Example 55 was repeated except that the strain of microorganism was changed as shown in Table 6 and (R,S)-(±)-3-isopropyl-5-acetoxymethyloxazolidin-2-one was employed as a substrate. The results are shown in Table 6.

TABLE 6

| | | Substrate: (R,S)—(±)-2-isopropyl-5-acetoxymethyloxazolidin-2-one | | | |
|---|---|---|---|---|---|
| | | (S)—(+)-3-isopropyl-5-acetoxymethyloxazolidin-2-one | | (S)—(+)-3-isopropyl-5-hydroxymethyloxazolidin-2-one | |
| Example | Strain | Yield g | $[\alpha]_D^{20}$ (C = 1.0, chloroform) | Yield g | $[\alpha]_D^{20}$ (C = 1.0, chloroform) |
| 57 | *Streptomyces flavovirens* IFO 3412 | 16.6 | +26.9° | 9.9 | +34.4° |
| 58 | *Streptomyces aureus* IFO 3175 | 16.2 | +19.6° | 9.8 | +25.1° |

EXAMPLE 59

The medium of the following components was prepared, and 400 ml portions thereof were separately placed in a 2 l of a Sakaguchi flask and steam-sterilized at 120° C. for 15 minutes.

| [Medium components] | |
|---|---|
| Glucose | 4.0% |
| Yeast extract | 0.3% |
| Meat extract | 0.3% |
| Peptone | 0.3% |
| (NH4)2HPO4 | 0.2% |
| KH2PO4 | 0.1% |
| pH | 7.0 |

On the other hand, *Enterobacter aerogenes* IFO 12010 had been previously cultured in the medium containing the same components as described above, and then 10 portions thereof were separately inoculated into the above medium and cultured with shaking at 30° C. for 24 hours. The cells were collected from 4 liters of the cultured broth by centrifugation and the cells were suspended in 400 ml of 0.1M phosphate buffer of pH 7.0, and 40 g of (R,S)-(±)-3-t-butyl-5-benzoyloxymethyloxazolidin-2-one having the formula:

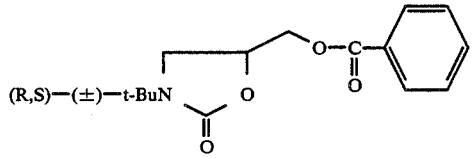

was added to the suspension as a substrate. The thus obtained mixture was subjected to reaction with stirring at 30° C. for 40 hours while adjusting a pH of the mixture in the range of 5 to 7 with a sodium hydroxide solution. After completing the reaction, the supernatant obtained by centrifugation was extracted with 400 ml of toluene to give unreacted (S)-(+)-3-t-butyl-5-benzoyloxymethyloxazolidin-2-one, and the resulting extract was concentrated under a reduced pressure.

Into 200 ml of 0.1M phosphate buffer was suspended the obtained concentrate and added 2 g of lipase (steapsin). The mixture was hydrolyzed with stirring at 30° C. for 18 hours while adjusting a pH of the mixture in the range of 5 to 7 with a sodium hydroxide solution.

After completing the hydrolysis, the mixture was extracted with 400 ml of ethyl acetate, and the extract was dehydrated, and then concentrated under a reduced pressure. When hexane was added to the concentrate, a colorless crystal was allowed to precipitate. The precipitated crystal was gathered and dried under vacuum to give 12.8 g of (S)-(+)-3-t-butyl-5-hydroxymethyloxazolidin-2-one having a specific optical rotatory power of $[\alpha]_D^{16}+46.1°$ (C=1.0, chloroform).

EXAMPLE 60 TO 74

The procedure of Example 59 was repeated except that the strain of microorganism and the substrate were changed as shown in Table 7, respectively. The results are shown in Table 7.

TABLE 7

| | | | Substrate (R,S)—(±)X—N | Product (S)—(+)X—N | | |
|---|---|---|---|---|---|---|
| Example | Strain | | X | Y | Yield g | $[\alpha]_D^{**}$(C = 1.0, chloroform) |
| 60 | *Enterobacter aerogenes* | IFO 12010 | t-butyl | trifluoromethyl | 10.9 | +45.1° |
| 61 | " | | " | dichloromethyl | 11.2 | +45.6° |
| 62 | " | | " | benzyl | 11.5 | +45.9° |
| 63 | " | | isopropyl | phenyl | 11.6 | +54.2° |
| 64 | " | | " | trifluoromethyl | 10.5 | +53.5° |
| 65 | " | | " | dichloromethyl | 11.0 | +53.9° |
| 66 | " | | " | benzyl | 11.1 | +54.1° |
| 67 | *Klebsiella pneumoniae* | IFO 3318 | t-butyl | phenyl | 12.0 | +45.2° |
| 68 | " | | " | trifluoromethyl | 11.0 | +45.0° |
| 69 | " | | " | dichloromethyl | 11.2 | +45.2° |
| 70 | " | | " | benzyl | 11.4 | +45.7° |
| 71 | " | | isopropyl | phenyl | 11.7 | +54.5° |
| 72 | " | | " | trifluoromethyl | 11.0 | +53.9° |
| 73 | " | | " | dichloromethyl | 9.8 | +53.2° |
| 74 | " | | " | benzyl | 10.1 | +54.0° |

**When X is t-butyl, a specific optical rotatory power was measured at 16° C., and when X is isopropyl, at 20° C.

EXAMPLE 75

*Enterobacter aerogenes* IFO 12010 was cultured in the same manner as in Example 1 to give 400 ml of cultured broth. To the culture broth was added 40 g of (R,S)-(±)-3-t-butyl-5-acetoxymethyloxazolidin-2-one having the formula:

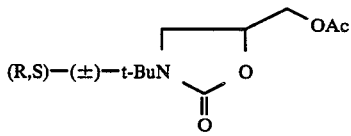

as a substrate. The resulting mixture was subjected to reaction in 1 l of a vessel with aerobically stirring at 30° C. for 18 hours while adjusting a pH of the mixture in the range of 5 to 7 with a sodium hydroxide solution. After completing the reaction, the reaction mixture was treated in the same manner as in Example 1 to give 1.03 g of (S)-(+)-3-t-butyl-5-hydroxymethyloxazolidin-2-one having a specific optical rotatory power of $[\alpha]_D^{16} + 43.9°$ (C=1.0, chloroform).

EXAMPLE 76 TO 78

The procedure of Example 75 was repeated except that the strain of microorganism and the substrate were changed as shown in Table 8, respectively. The results are shown in Table 8.

EXAMPLE 79

*Enterobacter aerogenes* IFO 12010 was inoculated into 10 ml of a culture medium containing 7% glucose, 0.3% yeast extract, 0.3% meat extract, 0.3% peptone, 0.2% $(NH_4)_2HPO_4$, 0.1% $KH_2PO_4$ of pH 7.0, and they were cultured with shaking at 30° C. for 24 hours.

Into 400 ml of the above culture medium was inoculated the above cultured broth and added simultaneously 4.0 g of (R,S)-(±)-3-t-butyl-5-acetoxymethyloxazolidine-2-one having the formula:

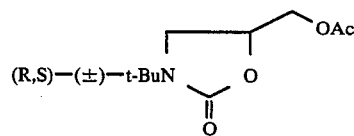

as a substrate, and the culture was carried out at 30° C. for 48 hours with shaking.

After completing the reaction, the reaction mixture was treated in the same manner as in Example 1 to give 0.82 g of (S)-(+)-3-t-butyl-5-hydroxymethyloxazolidin-2-one having a specific optical rotatory power of $[\alpha]_D^{16} + 41.5°$ (C=1.0, chloroform).

EXAMPLES 80 TO 82

The procedure of Example 79 was repeated except that the strain of microorganism and the substrate were changed as shown in Table 9, respectively. The results are shown in Table 9.

TABLE 9

| Example | Strain | | X | Y | Yield g | $[\alpha]_D^{**}$ (C = 1.0, chloroform) |
|---|---|---|---|---|---|---|
| 80 | *Enterobacter aerogenes* | IFO 12010 | isopropyl | methyl | 0.90 | +48.6° |
| 81 | *Klebsiella pneumoniae* | IFO 3318 | t-butyl | methyl | 0.75 | +41.2° |
| 82 | " | | isopropyl | methyl | 0.81 | +47.9° |

**the same as shown in Table 7

EXAMPLE 83

*Enterobacter aerogenes* IFO 12010 was cultured in the same manner as in Example 1 to give 4 l of cultured broth and the cultured broth was subjected to centrifugation to collect cells. The cells were suspended in 400 ml of 0.1M phosphate buffer of pH 7.0, homogenized with a Broun homogenizer under cooling, and then centrifuged to give a cell-free enzyme extract. To the resulting cell-free enzyme extract was added 4.0 g of (R,S)-(±)-3-t-butyl-5-acetoxymethyloxazolidin-2-one as a substrate, and the mixture was subjected to reaction with stirring at 30° C. for 18 hours while adjusting a pH of the mixture in the range of 5 to 7 with a sodium hydroxide solution. The reaction mixture was concen-

TABLE 8

| Example | Strain | | X | Y | Yield g | $[\alpha]_D^{**}$ (C = 1.0, chloroform) |
|---|---|---|---|---|---|---|
| 76 | *Enterobacter aerogenes* | IFO 12010 | isopropyl | methyl | 1.00 | +52.5° |
| 77 | *Klebsiella pneumoniae* | IFO 3318 | t-butyl | methyl | 0.99 | +44.5° |
| 78 | " | | isopropyl | methyl | 0.96 | +52.9° |

**the same as shown in Table 7 trated under a reduced pressure, the resulting concentrate was applied to a column of silica gel, and then treated in the same manner as in Example 1 to give 1.07 g of (S)-(+)-3-t-butyl-5-hydroxymethyloxazolidin-2-one having a specific optical rotatory power of $[\alpha]_D^{16}+46.3°$ (C=1.0, chloroform).

EXAMPLES 84 TO 94

The procedure of Example 83 was repeated except that the strain of microorganism and the substrate were changed as shown in Table 10, respectively. The results are shown in Table 10.

thyloxazolidin-2-one were added to 40 ml of 0.1M phosphate buffer of pH 7.0, and the mixture was incubated with stirring at 30° C. for 18 hours while adjusting a pH of the mixture in the range of 5 to 7 with a sodium hydroxide solution. After completing the hydrolysis, the reaction mixture was treated in the same manner as in Example 1 to give 1.1 g of (S)-(+)-3-t-butyl-5-hydroxymethyloxazolidin-2-one having a specific optical rotatory power of $[\alpha]_D^{16}+42.8°$ (C=1.0, chloroform).

EXAMPLES 96 TO 100

TABLE 10

| | | | Substrate | | Product | | |
|---|---|---|---|---|---|---|---|
| Example | Strain | | X | Y | Yield g | $[\alpha]_D^{**}$(C = 1.0, chloroform) | |
| 84 | *Enterobacter aerogenes* | IFO 12010 | isopropyl | methyl | 0.98 | +54.1° | |
| 85 | *Klebsiella pneumoniae* | IFO 3318 | t-butyl | methyl | 1.01 | +46.0° | |
| 86 | " | | isopropyl | methyl | 1.04 | +54.2° | |
| 87 | *Micrococcus luteus* | IFO 3064 | t-butyl | methyl | 1.10 | +41.8° | |
| 88 | " | | isopropyl | methyl | 0.95 | +49.4° | |
| 89 | *Pseudomonas cruciviae* | IFO 12047 | t-butyl | methyl | 1.00 | +37.3° | |
| 90 | " | | isopropyl | methyl | 1.05 | +41.7° | |
| 91 | *Alcaligenes faecalis* | IFO 12669 | t-butyl | methyl | 1.12 | +43.5° | |
| 92 | " | | isopropyl | methyl | 1.03 | +48.8° | |
| 93 | *Achromobacter parvulus* | IFO 13182 | t-butyl | methyl | 1.09 | +24.0° | |
| 94 | " | | isopropyl | methyl | 1.08 | +27.4° | |

**the same as shown in Table 7

EXAMPLE 95

One gram of L.P.L-Amano-3 (lipoprotein lipase: EC. 3.1.1.4., from Pseudomans; Amano Pharmaceutical Co., Ltd.) and 4.0 g of (R,S)-(±)-3-t-butyl-5-acetoxyme- The procedure of Example 95 was repeated except that (R,S)-(±)-3-isopropyl-5-acetoxymethyloxazolidin-2-one was employed as a substrate. The results are shown in Table 11.

TABLE 11

| | | | Substrate | |
|---|---|---|---|---|
| Example | Enzyme | (Origin) | X | Y |
| 96 | L. P. L-Amano-3 (Amano Pharmaceutical Co., Ltd.) | (*Pseudomonas*) | isopropyl | methyl |
| 97 | Lipase PL 266 | (*Alcaligenes*) | t-butyl | methyl |
| 98 | (Meito Sangyo Co., Ltd.) | | isopropyl | methyl |
| 99 | Lipase AL | (*Achromobacter*) | t-butyl | methyl |
| 100 | (Meito Sangyo Co., Ltd.) | | isopropyl | methyl |

| | Product | | | |
|---|---|---|---|---|
| Example | Yield g | $[\alpha]_D^*$(C = 1.0, chloroform) | Yield g | $[\alpha]_D^{**}$(C = 1.0, chloroform) |
| 96 | 1.67 | +40.1° | 1.12 | +51.1° |
| 97 | 1.62 | +34.9° | 1.01 | +44.5° |
| 98 | 1.64 | +41.2° | 1.09 | +52.4° |
| 99 | 1.70 | +18.8° | 1.10 | +23.9° |

TABLE 11-continued

| 100 | 1.16 | +21.1° | 1.04 | +27.3° |

**the same as shown in Table 7

What we claim is:

1. A process for producing an optically active (S)-(+)-3-alkyl-5-acyloxymethyloxazolidin-2-one which comprises subjecting a racemic compound (R,S)-(±)-3-alkyl-5-acyloxymethyloxazolidin-2-one having the formula:

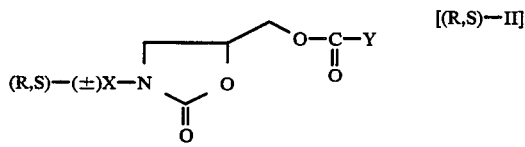

wherein X is a lower alkyl group and Y is a substituted or unsubstituted alkyl group, an alkenyl group, or a substituted or unsubstituted aromatic hydrocarbon group, to the action of a microorganism or an enzyme derived from said microorganism, said microorganism being selected from the group consisting of Enterobacter, Klebsiella, Micrococcus, Citrobacter, Escherichia, Pseudomonas, Staphylococcus, Alcaligenes, Achromobacter, Streptomyces, Candida, Debaryomyces, Endomyces, Hansenula, Geotrichum, Kluyveromyces, Metschnikowia and Pichia and having a stereoselective esterase activity capable of asymmetrically hydrolyzing the compound (R)-(−)-3-alkyl-5-acyloxymethyloxazolidin-2-one having the formula:

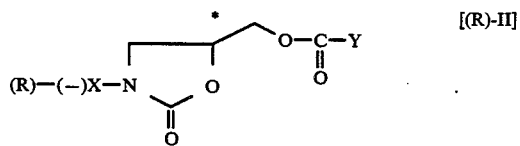

wherein X and Y are as heretofore defined to produce an optically active (R)-(−)-3-alkyl-5-hydroxymethyloxazolidin-2-one having the formula:

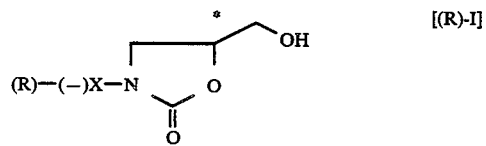

wherein X is as heretofore defined and isolating the unreacted optically active (S)-(+)-3-alkyl-5-acyloxymethyloxazoldin-2-one having the formula:

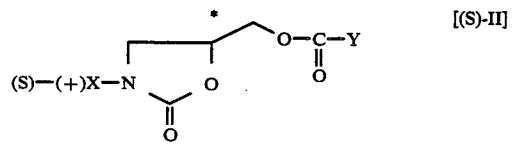

wherein X and Y are as heretofore defined from the produced optically active (R)-(−)-3-alkyl-5-hydroxymethyl-oxazolidin-2-one.

2. The process of claim 1, wherein X is t-butyl group or isopropyl group.

3. The process of claim 1, wherein the microorganism is cultured and reacted in a medium containing the compound [(R,S)-II] at a pH of from 4 to 8.

4. The process of claim 1, wherein the compound [(S)-II] is isolated from the produced compound [(R)-I] and organic acid by extracting the reaction mixture with an organic solvent.

5. The process of claim 1, wherein the compound [(S)-II] is separated from the produced compound [(R)-I] and organic acid by subjecting the reaction mixture to column chromatography.

6. The process of claim 1, wherein the compound [(S)-II] is isolated from the produced compound [(R)-I] and organic acid by fractional distillation of the reaction mixture.

7. The process of claim 1, wherein said microorganism is a member selected from the group consisting of Enterobacter aerogenes, Enterobacter cloacae, Klebsiella pneumoniae, Micrococcus luteus, Citrobacter freundii, Escherichia coli, Pseudomonas cruciviae, Pseudomonas fluorescens, Staphylococcus aureus, Alcaligenes faecalis, Achromobacter parvulus, Streptomyces flavovirens, Streptomyces aureus, Candida pseudotropicalis, Candida kefyr, Debaryomyces hansenii, Endomyces geotrichum, Hansenula anomala, Hansenula minuta, Geotrichum candidum, Kluyveromyces fragilis, Metschnikowia pulcherrima, Pichia farinosa and Pichia membranaefaciens.

8. The process of claim 1, wherein the compound [(R,S)-II] is subjected to the action of the microorganism in a culture medium or of a cell suspension prepared by separating cells from said culture medium.

9. The process of claim 1, wherein said enzyme is obtained from a cell-free extract prepared by homogenizing the cells of said microorganism, or said enzyme is obtained by fractionating said cell-free extract with ammonium sulfate.

10. The process of claim 1, wherein the compound [(R,S)-II] is subjected to the action of said enzyme at a temperature of from 10° to 50° C. and a pH of from 4 to 8.

11. A process for producing an optically active (S)-(+)-3-alkyl-5-hydroxymethyloxazolidin-2-one which comprises subjecting a racemic compound (R,S)-(±)-3-alkyl-5-acyloxymethyloxazolidin-2-one having the formula:

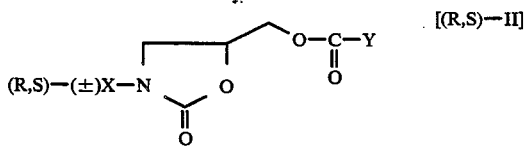

wherein X is a lower alkyl group and Y is a substituted or unsubstituted alkyl group, an alkenyl group, or a substituted or unsubstituted aromatic hydrocarbon group, to the action of a microorganism or an enzyme derived from said microorganism, said microorganism being selected from the group consisting of Enterbacter, Klebsiella, Micrococcus, Citrobacter, Escherichia, Pseudomonas, Staphylococcus, Alcaligenes, Achromobacter, Streptomyces, Candida, Debaryomyces, Endomyces, Hansenula, Geotrichum, Kluyveromyces, Metschnikowia and Pichia and having a stereoselective esterase activity capable of asymmetrically hydrolyzing the compound (R)-(—)-3-alkyl-5-acyloxymethyloxazolidin-2-one having the formula:

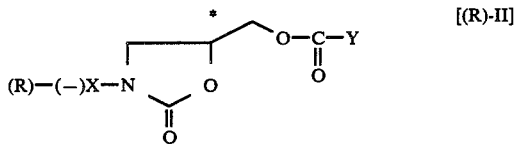

wherein X and Y are as heretofore defined to produce an optically active (R)-(—)-3-alkyl-5-hydroxymethyloxazolidin-2-one having the formula:

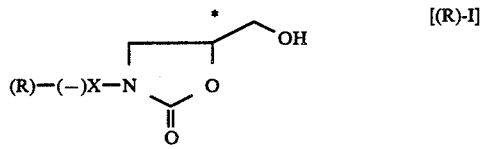

wherein X is as heretofore defined and isolating the unreacted optically active (S)-(+)-3-alkyl-5-acyloxymethyloxazoldin-2-one having the formula:

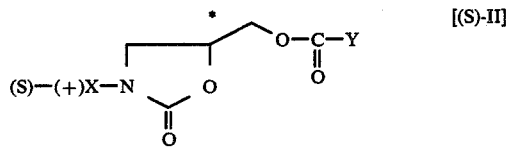

wherein X and Y are as heretofore defined from the produced compound [(R)-I], and hydrolyzing the compound [(S)-II] to give the optically active (S)-(+)-3-alkyl-5-hydroxymethyloxazolidin-2-one having the formula:

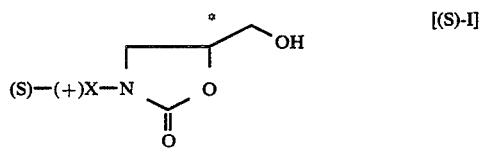

wherein X is as heretofore defined.

12. The process of claim 11, wherein X is t-butyl group or isopropyl group.

13. The process of claim 11, wherein the microorganism is cultured and reacted in a medium containing the compound [(R,S)-II] at a pH of from 4 to 8.

14. The process of claim 11, wherein the compound [(R,S)-II] is subjected to the action of said enzyme at a temperature of from 10° to 50° C. and a pH of from 4 to 8.

15. The process of claim 11, wherein the compound [(S)-II] is isolated from the produced compound [(R)-I] and organic acid by extracting the reaction mixture with an organic solvent.

16. The process of claim 11, wherein the compound [(S)-II] is separated from the produced compound [(R)-I] and organic acid by subjecting the reaction mixture to column chromatography.

17. The process of claim 11, wherein the compound [(S)-I] is prepared by chemically hydrolyzing the compound [(S)-II] at a pH of from 8 to 14.

18. The process of claim 11, wherein the compound [(S)-I] is prepared by enzymatically hydrolyzing the compound [(S)-II] with a hydrolase at a pH of from 4 to 8.

19. The process of claim 11, wherein said microorganism is a member selected from the group consisting of *Enterobacter aerogenes, Enterobacter cloacae, Klebsiella pneumoniae, Micrococcus luteus, Citrobacter freundii, Escherichia coli, Pseudomonas cruciviae, Pseudomonas fluorescens, Staphylococcus aureus, Alcaligenes faecalis, Achromobacter parvulus, Streptomyces flavovirens, Streptomyces aureus, Candida pseudotropicalis, Candida kefyr, Debaryomyces hansenii, Endomyces geotrichum, Hansenula anomala, Hansenula minuta, Geotrichum candidum, Kluyveromyces fragilis, Metschnikowia pulcherrima, Pichia farinosa* and *Pichia membranaefaciens*.

20. The process of claim 11, wherein the compound [(R,S)-II] is subjected to the action of the microorganism in a culture medium or of a cell suspension prepared by separating cells from said culture medium.

21. The process of claim 20, wherein said microorganism is cultured at a pH of from 3 to 11, and the compound [(RS)-II] is subjected to the action of the microorganism in the culture medium or to the cell suspension at a pH of from 4 to 8.

22. The process of claim 11, wherein said enzyme is obtained from a cell-free extract prepared by homogenizing the cells of said microorganism, or said enzyme is obtained by fractionating said cell-free extract with ammonium sulfate.

23. The process of claim 11, wherein the compound [(S)-II] is separated from the produced compound [(R)-I] and organic acid by fractional distillation of the reaction mixture.

* * * * *